United States Patent
Fagan et al.

[11] Patent Number: 5,858,007
[45] Date of Patent: Jan. 12, 1999

[54] HEMOSTATIC CATHETER INTRODUCER

[75] Inventors: John R. Fagan, Pepperell; John Zhang, Arlington, both of Mass.

[73] Assignee: C. R. Bard, Inc., Murray Hill, N.J.

[21] Appl. No.: 675,220

[22] Filed: Jul. 3, 1996

[51] Int. Cl.[6] .................................................. A61M 5/00
[52] U.S. Cl. ............................................ 604/256; 604/164
[58] Field of Search .................................... 604/256, 158, 604/164, 169, 167, 246

[56] References Cited

U.S. PATENT DOCUMENTS

| | | | |
|---|---|---|---|
| 4,000,739 | 1/1977 | Stevens | 128/214.4 |
| 4,424,833 | 1/1984 | Spector et al. | 137/849 |
| 4,430,081 | 2/1984 | Timmermans | 604/256 |
| 4,654,030 | 3/1987 | Moll et al. | 604/165 |
| 4,895,565 | 1/1990 | Hillstead | 604/167 |
| 4,917,668 | 4/1990 | Haindl | 604/167 |
| 4,931,042 | 6/1990 | Holmes et al. | 604/164 |
| 5,030,206 | 7/1991 | Lander | 604/164 |
| 5,180,365 | 1/1993 | Ensminger et al. | 604/93 |
| 5,242,413 | 9/1993 | Heiliger | 604/167 |
| 5,385,552 | 1/1995 | Haber et al. . | |
| 5,458,640 | 10/1995 | Gerrone | 604/264 |
| 5,613,663 | 3/1997 | Schmidt et al. | 251/149.2 |

FOREIGN PATENT DOCUMENTS 2284452  3/1993  United Kingdom .

*Primary Examiner*—Wynn Wood-Coggins
*Assistant Examiner*—Deborah Blyveis
*Attorney, Agent, or Firm*—Arthur Z. Bookstein; John F. Perullo

[57] ABSTRACT

A self-sealing hemostatic valve for use in a catheter apparatus is disclosed, comprising a proximal valve element having a sealing hole, a distal valve element having a flap and biasing means to enhance the force with which the flap bears against the distal side of the proximal valve element to normally seal the hole. The sealing hole seals about an instrument passed through the valve and the flap seals the valve when no instrument is present. The proximal face of the proximal valve element is provided with discontinuities that increase the flexibility of the proximal valve element in a distal direction.

15 Claims, 5 Drawing Sheets

HEMOSTATIC CATHETER INTRODUCER

FIELD OF THE INVENTION

This invention relates to improvements in hemostatic catheter introducers used in the insertion and removal of catheters and guidewires from a patient's blood vessel.

BACKGROUND OF THE INVENTION

It is common practice in many medical procedures, such as percutaneous transluminal angioplasty, to insert a guidewire, catheter, or other elongated instrument through a tubular catheter introducer that has been placed in the vasculature of a patient. The catheter introducer has a housing at its proximal end that has a self-sealing port through which the elongated instruments may be inserted, manipulated and removed. The seal typically is formed by a self-sealing valve through which the instrument is passed.

U.S. Pat. No. 4,430,081 to Timmermans describes a catheter introducer having a tubular shaft, a housing and a self-sealing, three-part, hemostatic flapper-type valve contained in the housing. The three-part valve has three disc-like elements sandwiched together including a first proximal disc having a slit, a second disc having a through-hole, and a third distal disc having a central flexible flap that overlies the hole. The first and second discs are said to effect a seal when an elongate device is passed through the valve. The third, distal disc cooperates with the second disc to effect a seal in the absence of an instrument passing through the device. In the latter mode, the device relies upon the patient's blood pressure to urge the flap of the third valve element against the hole in the middle disc. The effectiveness of the seal therefore depends in part on the fluid pressure within the housing, including the patient's blood pressure.

It often is desirable to aspirate a sample of the patient's blood through the introducer. For that purpose, a side port is provided on the housing distally of the valve. When the valve includes a flapper element, aspiration tends to draw the flap distally, away from the hole of the second valve element and potentially disrupting the seal. Air consequently could be drawn into the blood vessel, presenting risk of an air embolism. Blood leakage also could occur. Additionally, fluctuations in a patient's blood pressure similarly can cause variations in the effectiveness of the seal.

It is important that when a flapper-type of hemostatic valve is used the valve maintain its seal over a relatively wide range of pressures, including those reduced pressures that result from aspiration applied through the side port as well as fluctuations in a patient's blood pressure. It is therefore among the general objects of the invention to provide catheter introducers having an improved flapper-type of hemostatic valve that more effectively seals the lumen of the introducer over a wider range of pressures.

Also among the desirable features of a hemostatic catheter introducer is that the hemostatic valve should present as little drag as possible to an instrument passed through the introducer. In many procedures, it can be expected that the physician will rely on tactile feedback of the catheter when manipulating the catheter into a desired position. It is desirable to minimize the drag imposed on the instrument in order to maximize the tactile feedback. That objective typically conflicts with the ability of the device to form an effective seal about the instrument. It also is among the general objects of the invention to provide an improved hemostatic valve in which the drag imposed on the inserted instrument may be reduced.

SUMMARY OF THE INVENTION

One aspect of the invention relates to an improved catheter introducer having a self-sealing flapper-type valve in which means are provided to bias the flap against the adjacent face of the adjacent apertured valve element to enhance the seal. The valve includes an outer (proximal) valve element having a through-hole that seals about a longitudinal member extending through the valve, and an inner (distal) valve element in which the flap is formed. The flap covers the hole to seal the introducer when no instrument is present through the device. The biasing means may be integral to either or both the proximal or distal valve elements, or may be a separate element engageable with one or both of the two valve elements. The distal valve element also may be molded in a shape that provides a material memory to normally bias the flap against the distal face of the proximal valve element.

In another aspect of the invention, the proximal valve element is provided with discontinuities in the form of at least one circumferential slit formed in the proximal face of the valve element. The slit depth is such that a partial unslit thickness remains on the distal face of the proximal valve element to define a generally circular hinge associated with each slit. A plurality of such slits may be provided, defining a plurality of hinged rings surrounding the central hole. The hinged rings facilitate the flexibility of the proximal valve element in a distal direction when a catheter is passed through the device.

It is among the general objects of the invention to provide an improved self-sealing catheter introducer.

Another object of the invention is to provide an improved self-sealing flapper-type valve for a catheter introducer having enhanced ability to form an effective seal in the absence of a catheter extending through the device.

A further object of the invention is to provide an improved self-sealing flapper-type valve for a catheter introducer that provides an enhanced seal independently of the pressure within the introducer.

A further object of the invention is to provide a self-sealing flapper-type valve for a catheter introducer in which the flapper of the valve is biased against the hole that it seals by supplemental biasing means.

An additional object of the invention is to provide an improved hemostatic valve for a catheter introducer in which a proximal valve element includes a hole adapted to receive and form a seal about an inserted catheter and in which the proximal valve element displays increased flexibility in a distal direction.

BRIEF DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATIVE EMBODIMENT

Figure 1:
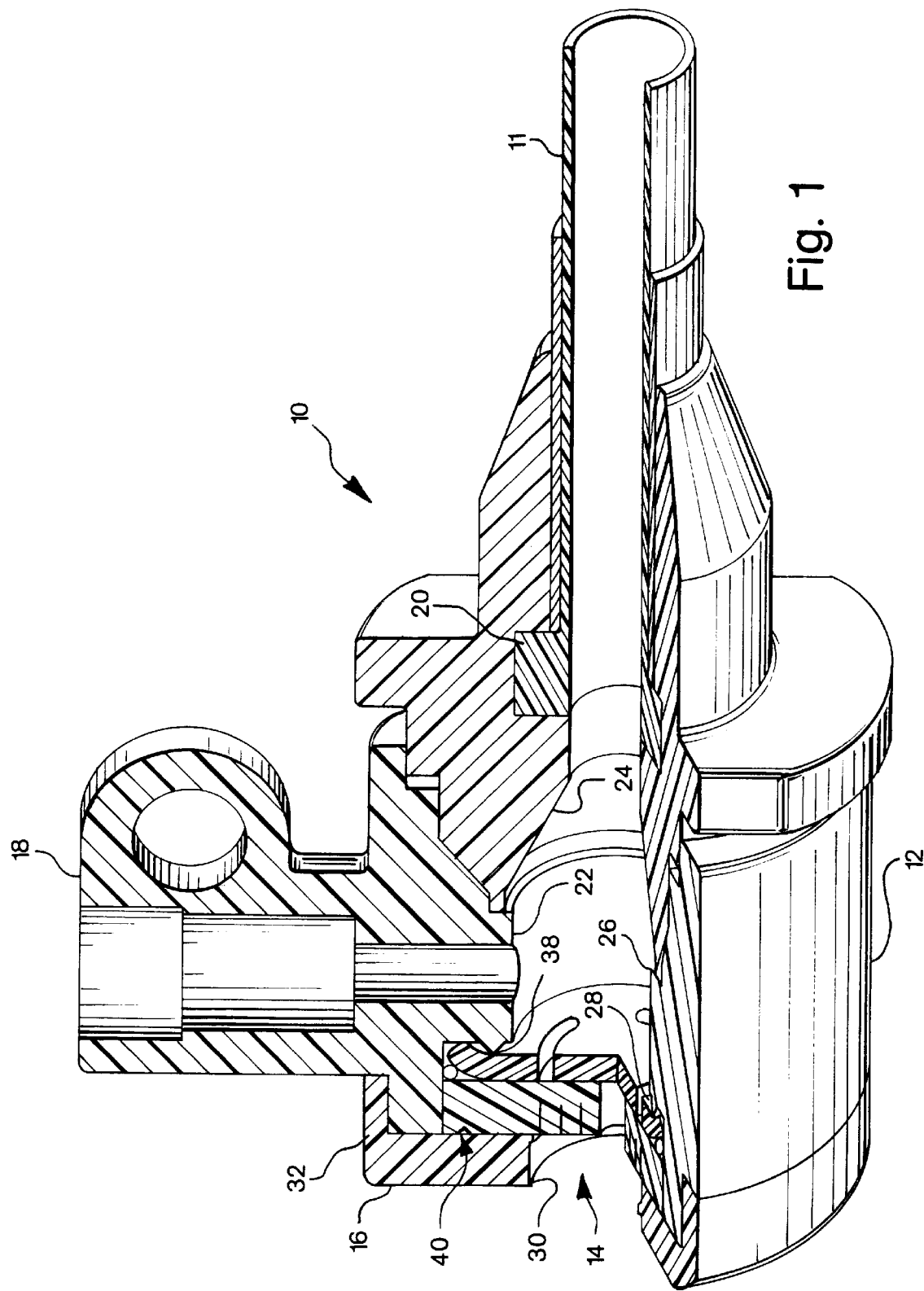
FIG. 1 is a broken-away illustration of a catheter introducer illustrating the internal structure of the housing and valve.

FIG. 1 shows a catheter introducer 10 that may incorporate the present invention. The introducer 10 includes an introducer tube 11 connected to and extending from a valve housing 12, and a two-piece, self-sealing valve 14 mounted within the valve housing 12. The valve 14 is retained firmly in place in the housing 12 by an end cap 16. The housing 12 has a side port 18 that communicates with the housing 12 distally of the valve 14.

The introducer tube 11, preferably formed from a fluorinated polymer, includes an enlarged head portion 20 to and about which the housing 12 can be molded directly and securely. The housing 12 has a hollow interior 22 that includes a distally tapering configuration, indicated at 24, that merges smoothly with the tapering inlet end of the head portion 20 of the introducer tube 11. The side port 18 is molded integrally with the housing 12 to communicate directly with the hollow interior 22 of the housing 12.

The hollow interior of the 22 of the housing 12 defines a cylindrical inner bore 26 that terminates in an enlarged diameter shoulder 28. The shoulder 28 terminates in an enlarged diameter outer bore 30 that receives the end cap 16. The end cap 16 has an inner portion dimensioned to fit snugly within the outer bore 30. The end cap 16 includes an outer peripheral collar 32 that engages the outer end of the housing 12 to determine and limit precisely the extent to which the distal end of the end cap 16 extends into the outer bore 30.

As shown in FIG. 1, the self-sealing valve 14 is retained between the end cap 16 and the shoulder 28 of the housing 12. The shoulder 28 preferably has a circular ridge 38 and there is an identical second circular ridge 40 on the distally facing surface of the distal end of the end cap 16. As shown in further detail in FIGS. 3 and 4, when the end cap 16 is fully seated, as determined by engagement of the collar 32 with the proximal end of the housing 12, the ridges 38 and 40 engage to firmly grip the valve 14.

Figure 2:
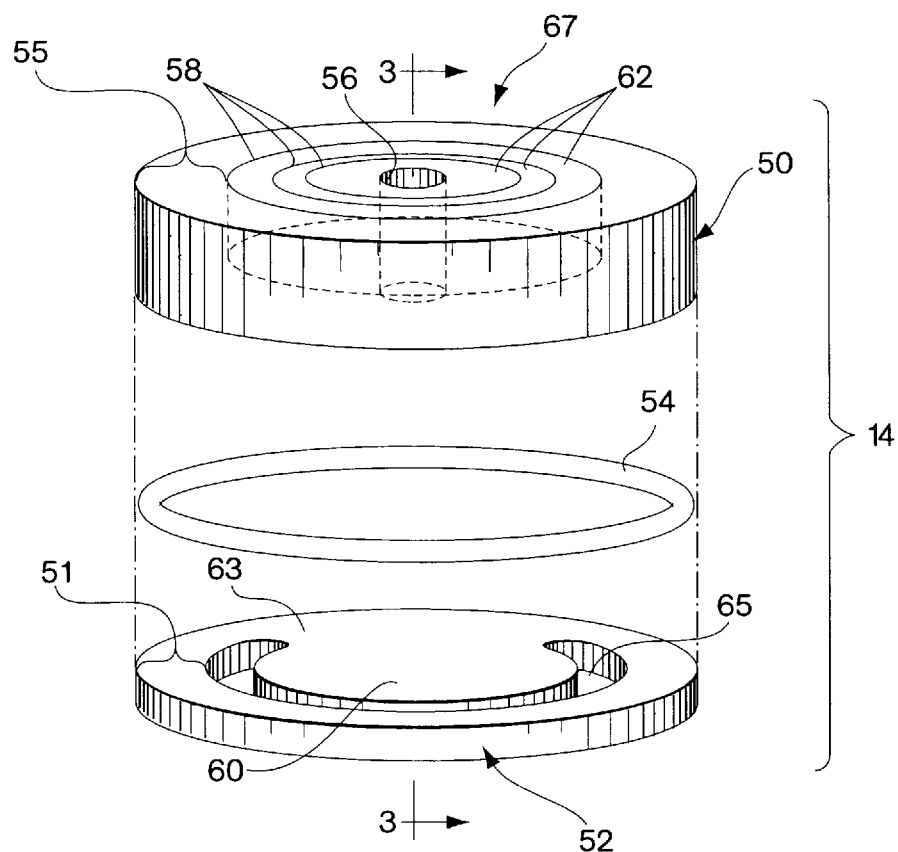
FIG. 2 is an exploded view of one embodiment of the self-sealing valve.

FIG. 2 shows an exploded view of one embodiment of the valve 14. The valve 14 includes a disc-like proximal valve element 50 that seals about an instrument passed through the valve 14, a disc-like distal valve element 52 that includes a flapper 60 that cooperates with the proximal valve element 50 to seal the introducer 10 in the absence of an instrument, and a biasing ring 54 to enhance the seal formed by the flapper 60, as described below.

Figure 3:
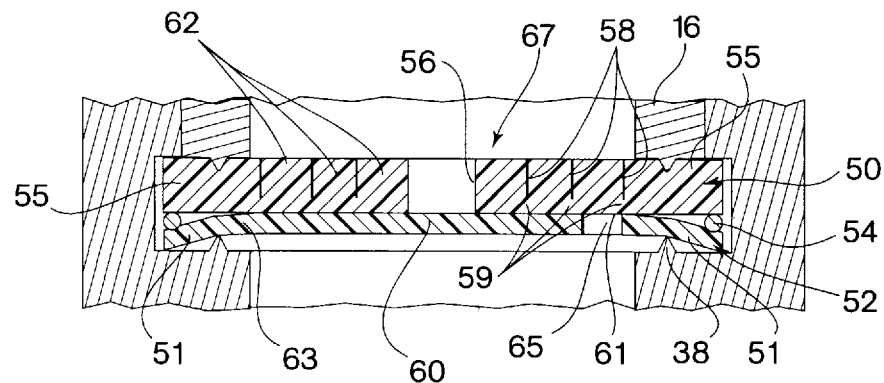
FIG. 3 is a sectional view of the assembled self-sealing valve of FIG. 2 through its diameter with no elongated instrument passing through the valve.
Figure 4:
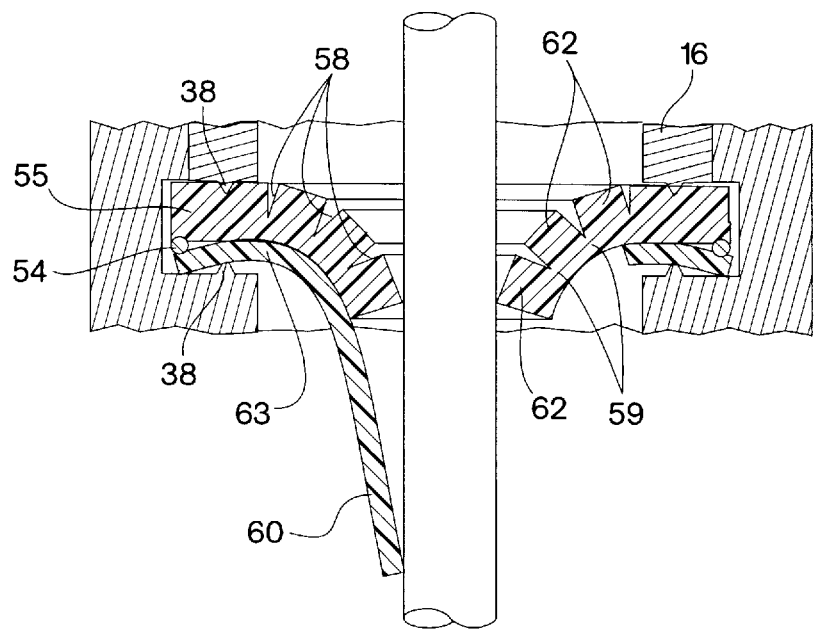
FIG. 4 is a sectional view similar to FIG. 3 with an elongated instrument passed through the valve.

The proximal valve element 50 has a central hole 56 arranged to receive and form a hemostatic seal about an elongate member passed through the hole 56. The diameter of the hole 56 may be selected to accommodate catheters or other like instruments within a desired range of diameters. As shown in FIGS. 2–4, the proximal valve element 50 is formed to define discontinuities to enhance the flexibility of the element 50 as a catheter or the like is inserted through the valve element 50. The discontinuity preferably is in the form of a plurality of circumferential rings 62 in its proximal face 67 by one or more circumferential slits 58 shown in FIG. 2 formed in the proximal face of the valve element 50 concentrically about the hole 56. The slits do not penetrate through the full thickness of the valve element 50 such that the unslit thickness may be considered as defining a series of circumferential, integral hinges 59 that connect the rings 62. The circumferential slits 58 increase the flexibility of the proximal element 50 in a distal direction. The drag on an instrument inserted through the proximal element 50 consequently may be reduced. The slits 58, however, should be formed in relation to the geometry and dimensions of and the material from which the valve element 50 is formed to avoid bowing of the proximal valve element 50 in the proximal direction in response to the systolic pulses of the patient's blood pressure.

The flapper 60, formed integrally with the distal valve element 52, is configured so that when the proximal and distal valve elements 50, 52 are retained in registry within the housing 12, the flapper will lie against the distal face 61 of the proximal valve element 50 in overlying relation to the aperture 56. The flap 60 includes a hinge portion 63 by which the flap 60 is integrally connected to the peripheral margin 51 of the distal valve element 52. The distal valve element 52 should be formed with a gap separation, indicated at 65 (FIG. 2), between the outer edge of the flap 60 and the inner edge of the peripheral margin 51 to enable the flap 60 to move freely without interference.

In one aspect of the invention, the proximal and distal valve elements 50, 52 are arranged so that the flap 60 will be biased normally against the distal face 61 of the proximal valve element 50, not only by the inherent resilience of the material from which it is formed, but also by a means to supplement the biasing force. In one embodiment, as shown in FIGS. 3 and 4, a biasing ring 54 is disposed between the outer margins 55, 51 of the proximal and distal valve elements 50, 52, radially outward of the ridge 38. When the device is assembled, the ring 54 is captured between the margins 51, 55 in cooperative arrangement with the ridge 38 to constrain the valve element 52 in a proximally bowed configuration (FIG. 3). By constraining the distal valve element 52 in a bowed configuration, the flap 60 can be biased against the distal face 61 of the proximal valve element 50 under a greater force than if element 52 were flat. The resulting additional biasing force enhances the seal provided by the flap 60 and enables a secure seal to be formed over a greater range of pressures within the valve housing in the absence of an instrument. As shown in FIG. 4, when an instrument is passed through the hole 56, the flap, and particularly its hinge region 63, should be sufficiently flexible to bend distally without imposing a significant additional drag on the inserted instrument.

The dimensions and materials from which the proximal and distal valve elements 50, 52 may be formed can be varied depending on the specific catheters or devices with which the device is to be used and to provide selected results. In each configuration, the distal valve element 52 should be sufficiently stiff to provide an enhanced bias against the aperture 56 yet be sufficiently flexible to enable an instrument to urge the flap 60 from its sealing engagement with the aperture 56. It is considered that in many applications, where the proximal and distal valve elements 50, 52 may be formed from similar or identical materials, the thickness of the distal valve element 52 may be reduced, as suggested in the drawings, in comparison to that of the proximal valve element 50.

The valve elements 50, 52 may be molded from a suitable material such as a silicone rubber. The stiffness of the material should be such as to assure that the flap 60 can be biased sufficiently against the distal face of the proximal valve element 50. By way of example, at least the distal element 52, and possibly also the proximal element 50 may be formed from a silicone rubber having a durometer in the upper regions of the Shore A hardness scale, for example, of the order of between 30 to 60 durometer Shore A. It should be understood, however, that the specific materials should be selected in conjunction with the geometry and dimensions of the components, including those of the hinge region of the flap 60. The valve elements 50, 52, may be lubricated with a suitable lubricant applied as part of the construction process or, alternately, the valve elements 50, 52 may be formed from an elastomeric material that has been impregnated with a lubricant such that the lubricant will tend to leach from the material to lubricate an instrument passed through the device. Lubricant impregnated silicone rubber components can be molded and may be available from Alps South Corporation of Tampa, Fla.

Figure 5:
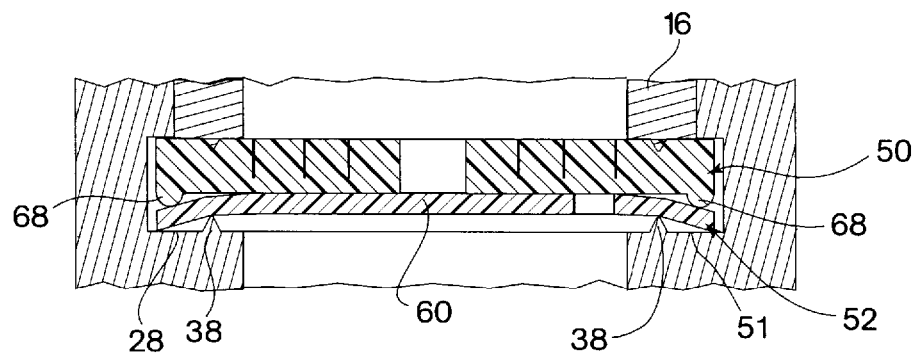
FIG. 5 is an illustration similar to FIG. 3 of a modified embodiment of the valving arrangement in which a biasing ring is formed integrally with the proximal valve element.
Figure 6:
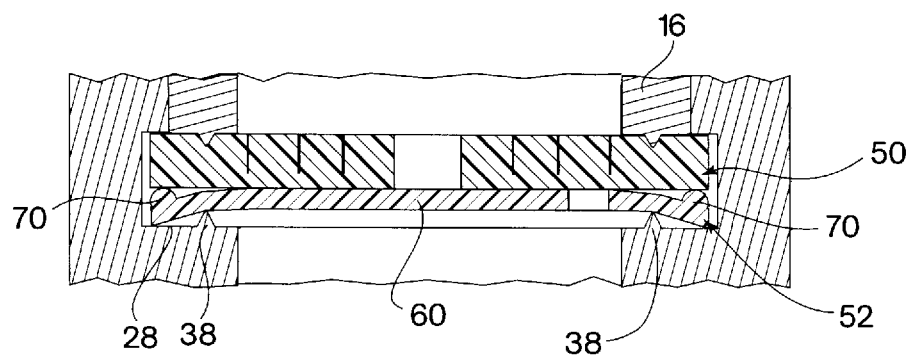
FIG. 6 is a sectional illustration similar to FIG. 3 illustrating a biasing ring formed integrally with the distal valve element.

The foregoing embodiment may be modified to incorporate the biasing ring integrally with one of the valve elements 50, 52. FIG. 5 shows a biasing ring 68 formed integrally with and projected from the distal face of the proximal valve element 50. The ring is dimensioned to be disposed about the annular ridge 38 in the housing so that when the device is assembled, the most peripheral region of the margin 51 will be pressed against the shoulder 28 and retained firmly below the level of the annular ridge 38. That will constrain the distal element in a somewhat dished configuration to enhance the bias of the flap 60 against the aperture 56. FIG. 6 illustrates an arrangement in which the biasing ring 70 is formed integrally with the proximal face of the distal valve element 52. The function and effect is the same as having ring 68 formed on element 50, or using ring 54 between elements 50, 52.

Figure 10:
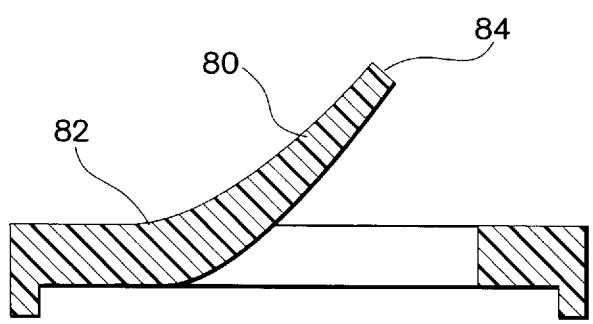
FIG. 10 is an illustration of a modified form of prebiased distal valve element similar to FIG. 8 but with a tapered flapper element.
Figure 7:
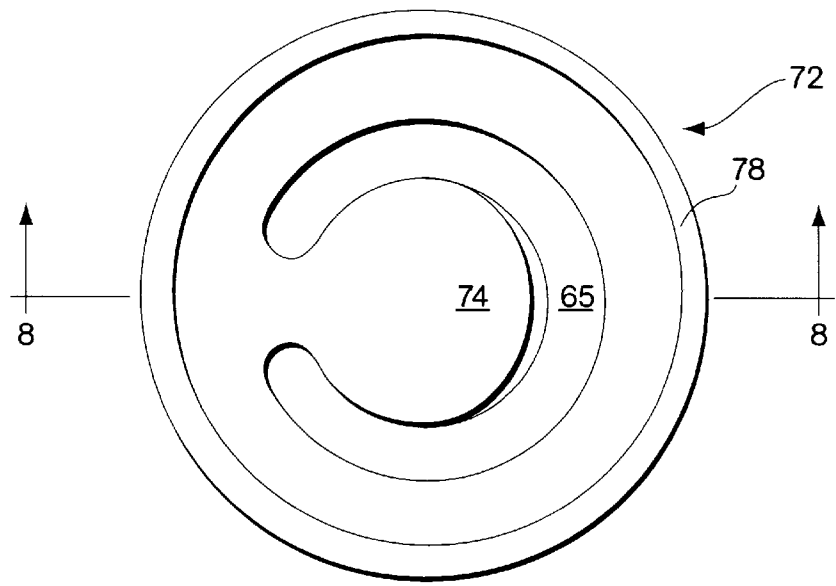
FIG. 7 is a plan illustration of the distal face of a modified embodiment of the distal valve element.
Figure 8:
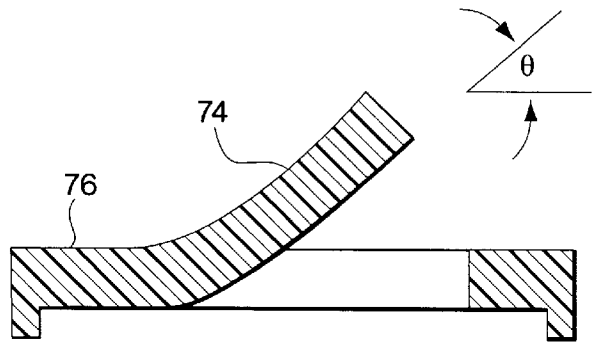
FIG. 8 is a sectional illustration of the distal valve element of FIG. 7 as seen along the line 8—8 of FIG. 7.
Figure 9:
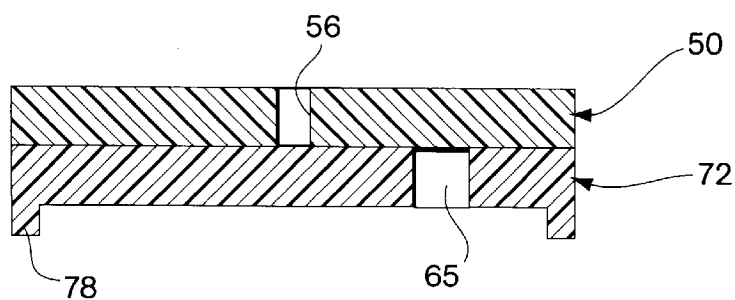
FIG. 9 is a sectional illustration of the distal valve element of FIG. 8 in face-to-face engagement with a proximal valve element.

FIGS. 7 and 8 illustrate another embodiment of the invention in which the distal valve element 72 is molded so that its flap 74, when relaxed, will protrude proximally out of the plane of the remaining portions of the valve element 72. The flap 74 may be arranged to project out of the plane of the proximal face 76 of the distal valve element 72 by an angle θ that may be, for example, between about 5° to 20°, or any other functioning angle that will develop the desired degree of bias. When the proximal and distal valve elements 50, 72 are brought together in flat face-to-face contact, as illustrated in FIG. 9, the flap 74 will have been urged from its relaxed, out-of-plane configuration of FIG. 8 to a stressed, in-plane configuration. The stressed flap 74 thus will bear against the distal face of the proximal valve element 50 under an enhanced force to enhance the seal. In this embodiment, it may be preferable to form the distal valve element 72 from a material having a higher durometer than that of the proximal element. The distal valve element 72 also may be provided with a peripheral flange 78 extending from its distal face. The flange may be received in a peripheral groove (not shown) formed in the shoulder 28 of the housing to further secure the device in the assembly. Such a flange is described in U.S. patent application Ser. No. 08/241,627 filed May 12, 1994. In another aspect of this embodiment, the flap may be tapered, as suggested in FIG. 10 at 80, in a direction from its hinge 82 to its free end 84. Such tapering may result in a more uniform applied stress of the flap along its length.

The foregoing arrangements for enhancing the effectiveness of catheter introducers may be used individually or in combinations, as desired. Thus, the biasing rings, out-of-plane flaps and retaining flanges may be combined to produce a desired degree of sealing performance.

It should be understood that the foregoing description of the invention is intended merely to be illustrative thereof and that other embodiments, modifications and equivalents may be apparent to those skilled in the art without departing from its spirit.

Having thus described the invention, what we desire to claim and secure by letters patent is:

1. A catheter introducer comprising:
   an elongate tubular sheath having proximal and distal ends;
   a valve housing having a proximal end, the housing being connected to the proximal end of the sheath, the valve housing having an aperture at its proximal end;
   a hemostatic valve disposed withing the valve housing and comprising a proximal valve element having proximal and distal faces and a central aperture;
   a distal valve element having proximal and distal faces and formed to define a flexible flap disposed to overlie the central aperture of the proximal valve element when the valve elements are in registry with each other;
   the valve elements being gripped within the housing about their peripheral margins to secure and constrain the distal valve element to urge the distal valve element in a bowed configuration so as to bias the flap against the distal face of the proximal element.

2. A catheter introducer as defined in claim 1 further comprising:
   the flap being biased toward the proximal valve element by a biasing member engageable with the peripheral margin of the distal valve element.

3. A catheter introducer as defined in claim 2 wherein the housing further comprises an inner bore and an outer bore, the outer bore being larger than the inner bore and defining a shoulder at the juncture of the inner bore and the outer bore, the shoulder in the housing being constructed and arranged to receive the peripheral margins of the valve elements;
   the shoulder having a proximally extending ridge adapted to engage the distally facing surface of the margin of the distal valve element, the ridge being generally circular and being spaced inwardly of the outer bore;
   the biasing member being disposed radially between the ridge and the outer bore.

4. A catheter introducer as defined in claim 3 wherein the biasing member is separate from the proximal and distal valve elements.

5. A catheter introducer as defined in claim 3 wherein the biasing member is formed integrally with the distal face of the proximal valve member.

6. A catheter introducer as defined in claim 3 wherein the biasing member is formed integrally with the proximal face of the distal valve element.

7. A catheter introducer comprising:
   an elongate tubular sheath having proximal and distal ends;
   a valve housing having a proximal end, the housing being connected to the proximal end of the sheath, the valve housing having an aperture at its proximal end;

a hemostatic valve disposed withing the valve housing and comprising a proximal valve element having proximal and distal faces and a central aperture;

a distal valve element oriented substantially along a defined plane and having proximal and distal faces and formed to define a flexible flap disposed to overlie the central aperture of the proximal valve element when the valve elements are in registry with each other;

the flap, when relaxed, projecting out of the plane of the distal valve element so that when the valve elements are in face-to-face contact, the flap will be biased forcefully against the distal face of the proximal valve element.

8. A catheter introducer as defined in claim 7 wherein the flap has a free end and is of reduced thickness toward its free end.

9. A catheter introducer comprising:

an elongate tubular sheath having proximal and distal ends;

a valve housing having a proximal end, the housing being connected to the proximal end of the sheath, the valve housing having an aperture at its proximal end;

a hemostatic valve disposed withing the valve housing and comprising a proximal valve element having proximal and distal faces and a central aperture, the proximal face of the proximal valve element formed to defined a discontinuity to increase the flexibility of the proximal valve element in a distal direction wherein the discontinuity comprises the proximal face of the proximal valve element being formed to include at least one circumferential slit about the central hole, the slit extending to a depth less than the thickness of the proximal valve element thereby to define an integral circumferential hinge at the unslit region associated with the slit, and at least one ring about the central aperture adapted to flex in a distal direction at the hinge;

a distal valve element having proximal and distal faces and formed to define a flexible flap disposed to overlie the central aperture of the proximal valve element when the valve elements are in registry with each other;

the valve elements being contained in the housing in registry with each other with the flap being biased toward the distal face of the proximal valve element.

10. In a catheter introducer having a hemostatic valve defined by at least two valve elements arranged to lie in face-to-face relation to each other, including an outermost valve element having a central aperture and a proximal face, the improvement comprising at least one circumferential slit formed in the proximal face of the outermost valve element, the slit extending only partly through the thickness of the proximal element thereby to define a circumferential hinge in the unslit region associated with the slit.

11. A catheter introducer as defined in claim 10 further comprising a plurality of said slits and hinges, the catheter introducer also including a plurality of rings.

12. A catheter introducer comprising:

an elongate tubular sheath having proximal and distal ends;

the a valve housing connected to proximal end of the sheath and having an aperture at its proximal end;

a hemostatic valve disposed within the valve housing and comprising a proximal valve element having proximal and distal faces and a central aperture;

a distal valve element having proximal and distal faces and formed to cooperate with the distal face of the proximal valve element to overlie and effect a seal of the central aperture;

the proximal face of the proximal valve element including a discontinuity to increase the flexibility of the proximal valve element in a distal direction, wherein the discontinuity comprises at least one circumferential slit formed in the proximal face of the proximal valve element about the central aperture.

13. A method for assembling a catheter introducer containing a hemostatic valve comprising:

providing a housing open at its proximal end and a cap to enclose the proximal end;

providing a proximal valve element and a distal valve element, the proximal valve element having a central aperture and the distal valve element having a flap, the flap extending proximally out of the plane of the distal valve element when the distal valve element is in a relaxed configuration;

constraining the proximal and distal valve elements within the housing by the cap such that the valve elements are in face-to-face relation with the flap bearing forcibly against the distal face of the distal valve element.

14. A catheter introducer comprising:

an elongate tubular sheath having proximal and distal ends;

a valve housing connected to the proximal end of the sheath and having an aperture at its proximal end;

a hemostatic valve disposed withing the valve housing and comprising a proximal valve element having proximal and distal faces and a central aperture;

a distal valve element oriented substantially along a defined plane and having proximal and distal faces and formed to define a flexible flap disposed to overlie the central aperture of the proximal valve element when the valve elements are in registry with each other;

wherein the flap, when relaxed, projects out of the plane of the distal valve element so that when the valve elements are in face-to-face contact, the flap will be biased forcefully against the distal face of the proximal valve element.

15. The catheter introducer as defined in claim 14 wherein the flap has a free end and is of reduced thickness toward its free end.

* * * * *